United States Patent
Lentner et al.

(10) Patent No.: US 9,987,146 B1
(45) Date of Patent: Jun. 5, 2018

(54) SPINAL IMPLANT WITH LATERAL EXPANDING COAXIAL DRIVE SYSTEM

(71) Applicant: Hammill Medical LLC, Palm Beach Gardens, FL (US)

(72) Inventors: Greg Lentner, Maumee, OH (US); John E. Hammill, Sr., Maumee, OH (US)

(73) Assignee: Hammill Medical LLC, Palm Beach Gardens, FL (US)

( * ) Notice: Subject to any disclaimer, the term of this patent is extended or adjusted under 35 U.S.C. 154(b) by 0 days. days.

(21) Appl. No.: 15/885,007

(22) Filed: Jan. 31, 2018

(51) Int. Cl.
*A61F 2/44* (2006.01)
*A61F 2/46* (2006.01)
*A61F 2/30* (2006.01)
*A61F 2/28* (2006.01)

(52) U.S. Cl.
CPC ............ *A61F 2/447* (2013.01); *A61F 2/4611* (2013.01); *A61F 2002/2835* (2013.01); *A61F 2002/30265* (2013.01); *A61F 2002/30556* (2013.01); *A61F 2002/30579* (2013.01); *A61F 2002/30622* (2013.01); *A61F 2002/30828* (2013.01)

(58) Field of Classification Search
CPC .................. A61F 2/447; A61F 2/4611; A61F 2002/2835; A61F 2002/30265; A61F 2002/30556; A61F 2002/30579; A61F 2002/30622; A61F 2002/30828
USPC ................. 623/17.11, 17.15, 17.16; 606/246
See application file for complete search history.

(56) References Cited

U.S. PATENT DOCUMENTS

| 2015/0012097 A1* | 1/2015 | Ibarra | A61F 2/447 623/17.15 |
| 2015/0366675 A1* | 12/2015 | Matthews | A61F 2/4425 623/17.16 |
| 2017/0333198 A1* | 11/2017 | Robinson | A61F 2/447 |

* cited by examiner

*Primary Examiner* — Pedro Philogene
*Assistant Examiner* — David C Comstock
(74) *Attorney, Agent, or Firm* — McHale & Slavin, P.A.

(57) ABSTRACT

A lateral expanding coaxial spinal implant. The system consists of a centrally located drive screw with lateral actuators. The actuators contain pins positioned through angular slots located on sidewalls attached to endplates. The angular slots provide angular positioning when the actuator pins translate through them. A carriage contains a drive screw for operating of the actuators. Alignment pins provided on each endplate allow the endplates to rotate laterally relative to the carriage. An adjustment nut is axially retained by the carriage, but allowed to rotate. To expand/contract the endplates, the drive screw and adjustment nut are rotated together, with no relative motion between them. To change the angle of the endplates, the drive screw is rotated.

11 Claims, 17 Drawing Sheets

SECTION 6-6

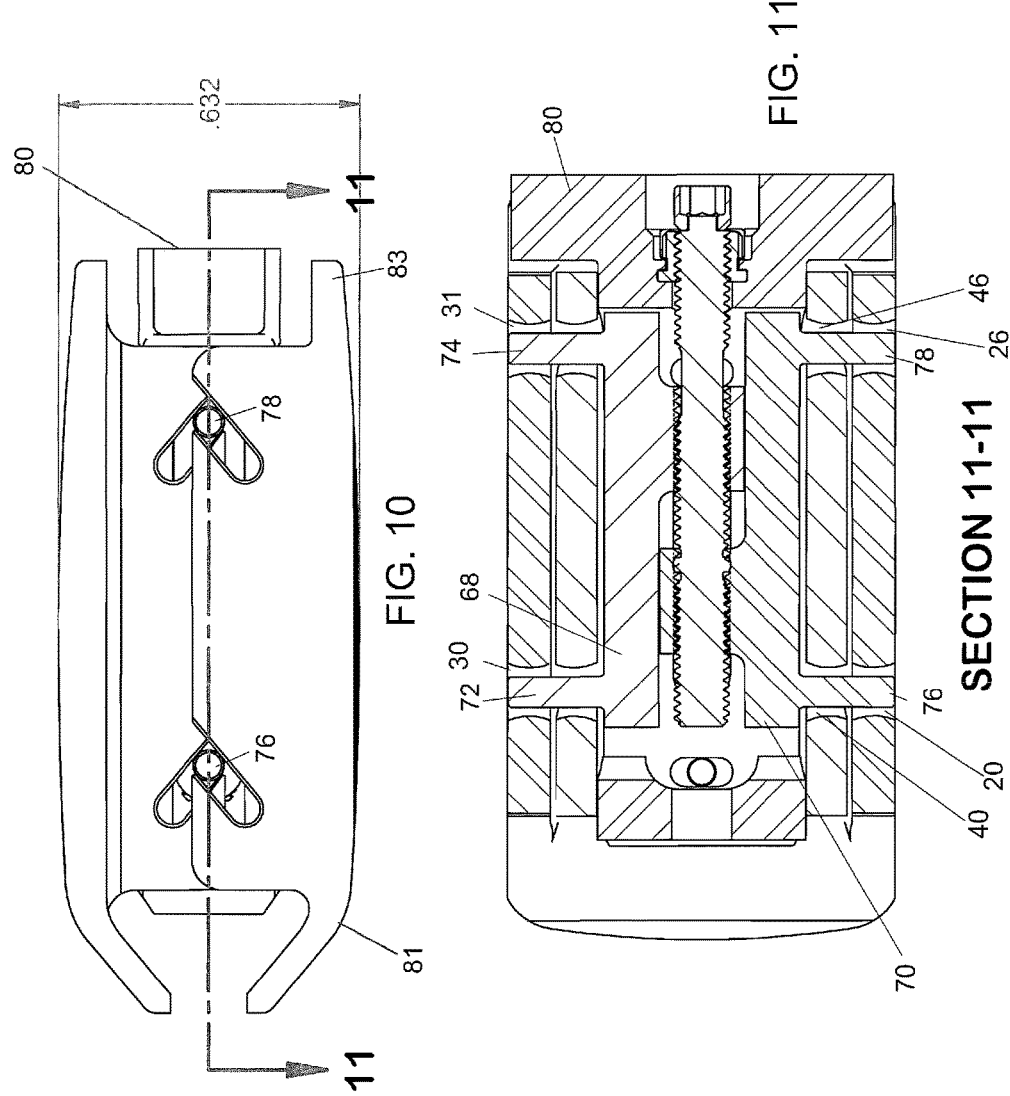

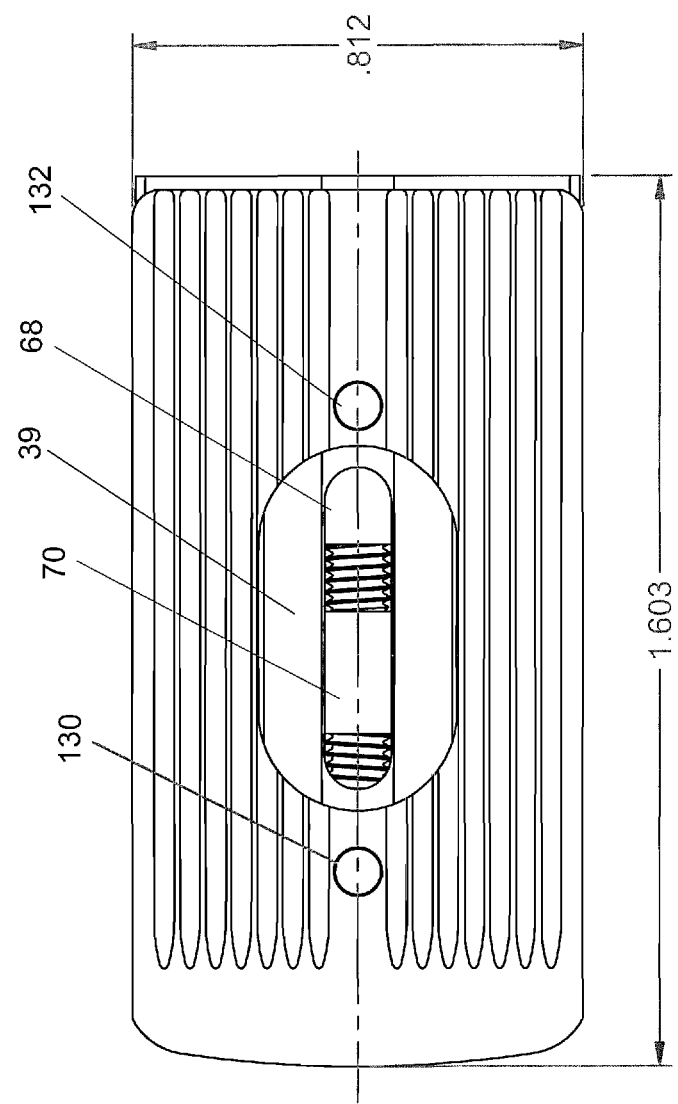

SECTION 14-14

SECTION 16-16

SECTION 23-23

# US 9,987,146 B1

SPINAL IMPLANT WITH LATERAL EXPANDING COAXIAL DRIVE SYSTEM

RELATED APPLICATIONS

This application is related to U.S. patent application Ser. No. 15/827,735, filed Nov. 30, 2017.

FIELD OF THE INVENTION

This invention is directed to the field of spinal implants, namely a spinal implant with a lateral expanding coaxial drive system.

BACKGROUND OF THE INVENTION

Back pain affects every human to some extent. Causes of back pain can result from a number of issues, one of which is the rupture or degeneration of intervertebral discs due to aging, disease, herniations or trauma. Left untreated, the failure of a disc can lead to compression on the spinal cord or cauda equian. Many types of spinal irregularities can cause pain, limit range of motion, or injure the nervous system within the spinal column. These irregularities can leave the individual with numbness, pain, and weakness or in a state of permanent disability.

Spinal stabilization is an accepted method in alleviating chronic back pain caused by disabled disk material or excessive movement of individual vertebrae. Conventional stabilization techniques include fusing two or more vertebrae together to circumvent or immobilize the area to eliminate disc movement. Generally, spinal fusion procedures involve removing some or all of the diseased or damaged disc, and inserting one or more intervertebral implants into the resulting disc space. Many irregularities can be treated by immobilizing the failing disc or performing a discectomy. For example, treatment can include removal and replacement of an affected intervertebral disc with a prosthesis. For instance, the vertebral disk material which separates the vertebrae can be removed and bone graft material inserted into the space for interbody fusion. In addition to, or in place of, the bone graft material, a spinal implant may be inserted in the intervertebral space.

In certain applications, it is beneficial that a device is used which is capable of fitting within a confined space, wherein the device can be further adjusted in height and angular adjustment from one side to the other.

SUMMARY OF THE INVENTION

Disclosed is a lateral expanding coaxial drive spinal implant consisting of a centrally located drive screw for use in expanding endplates, and causing lateral angular movement of the endplates. The drive screw employs a carriage for aligning actuators having matching threads. The actuators contain pins which are positioned through angular slots located in each endplate. The angular slots allow for separating of the endplates, as well as angular positioning when the actuator pins translate through them. The carriage further houses fixed pins to create an axis point on the endplates, limiting any axial movement of the endplates. An adjustment nut is situated at the end of the carriage and threaded on the drive screw. The nut is axially retained by the carriage, but allowed to rotate. To expand/contract the endplates, the drive screw and adjustment nut are rotated together with no relative motion between them. To change the angle of the endplates, the adjustment nut is rotated, moving the actuators in opposing directions to cause a tipping of the endplates.

An objective of the invention is to teach a spinal implant constructed and arranged to fit in a confined space with height adjustment and angular adjustment from one side to the other.

Another objective of the invention is to teach a device for insertion into a confined space, wherein the height of the device is adjusted by rotation of a drive screw and adjustment nut simultaneously, and angular adjustment of the implant is performed by rotation of an adjustment nut.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 10 is a side view thereof;
FIG. 11 is a cross sectional view of FIG. 10 taken along section line 11-11;
FIG. 12 is a top view thereof.

DETAILED DESCRIPTION OF THE PREFERRED EMBODIMENT

Figure 1:
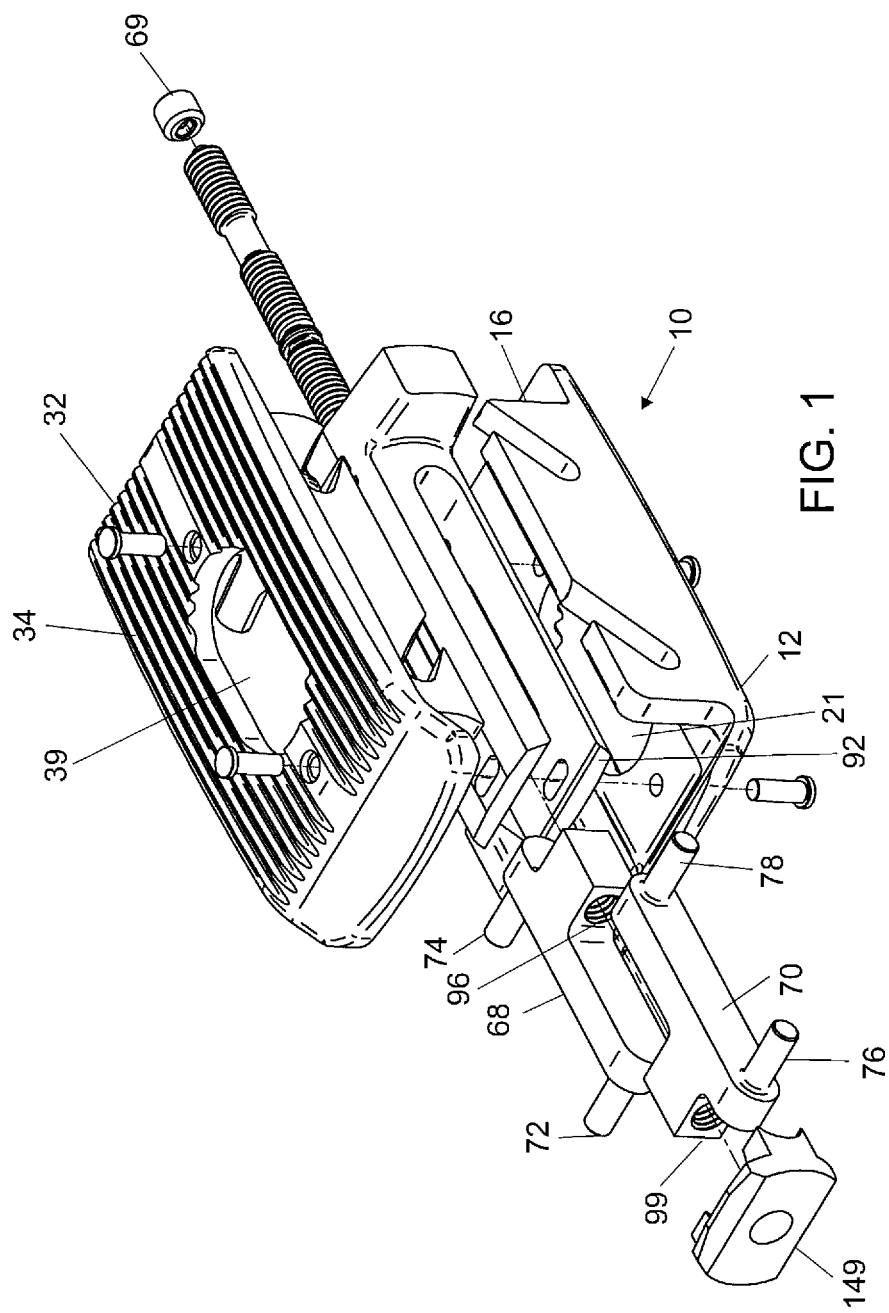
FIG. 1 is a frontal facing perspective exploded view of the spinal implant.
Figure 2:
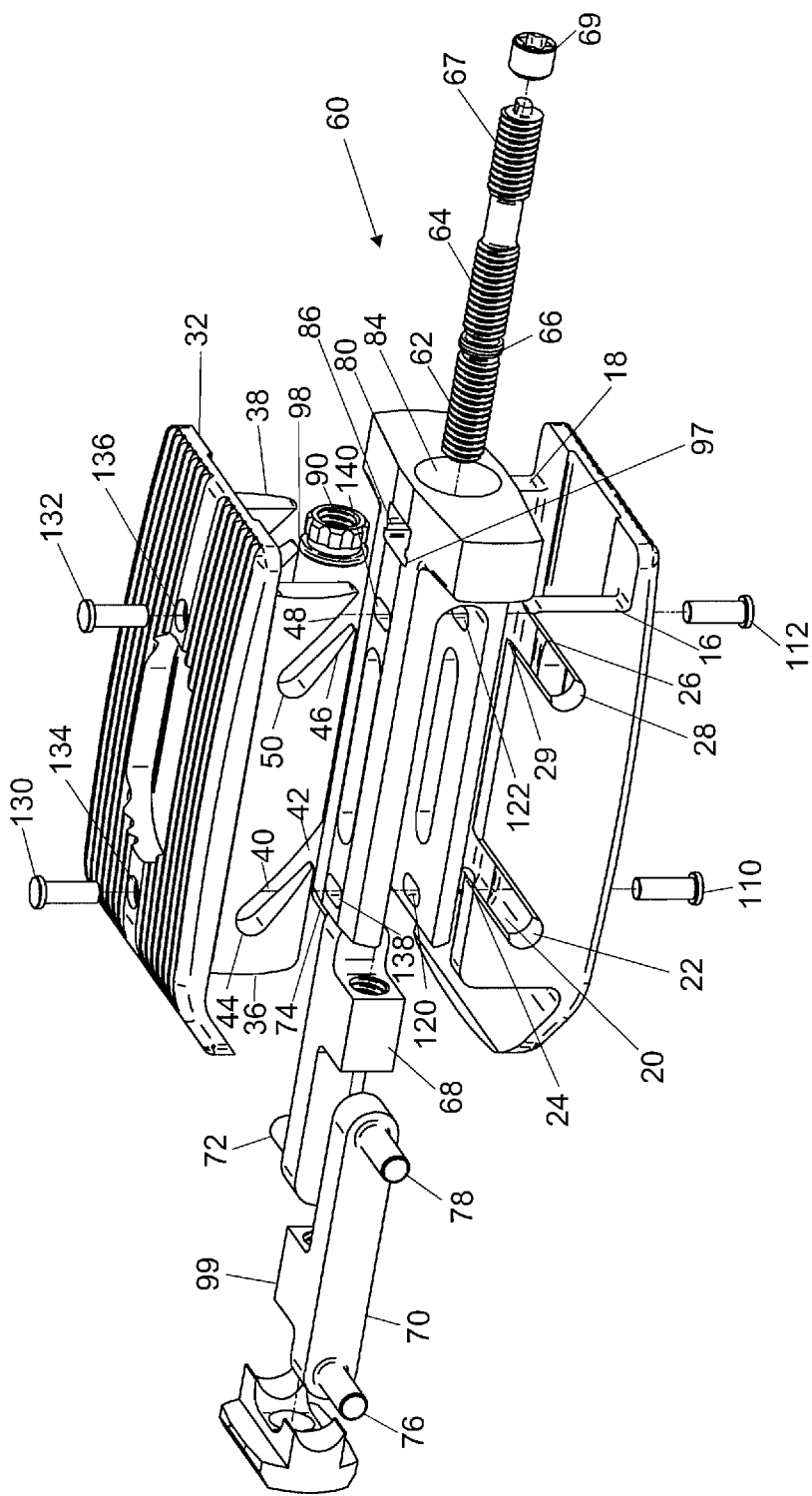
FIG. 2 is a rearward facing perspective exploded view.
Figure 3:
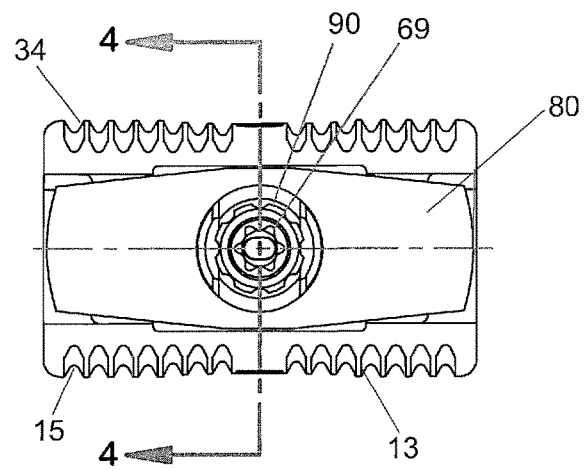
FIG. 3 is an end view of the spinal implant in a compressed position.
Figure 4:
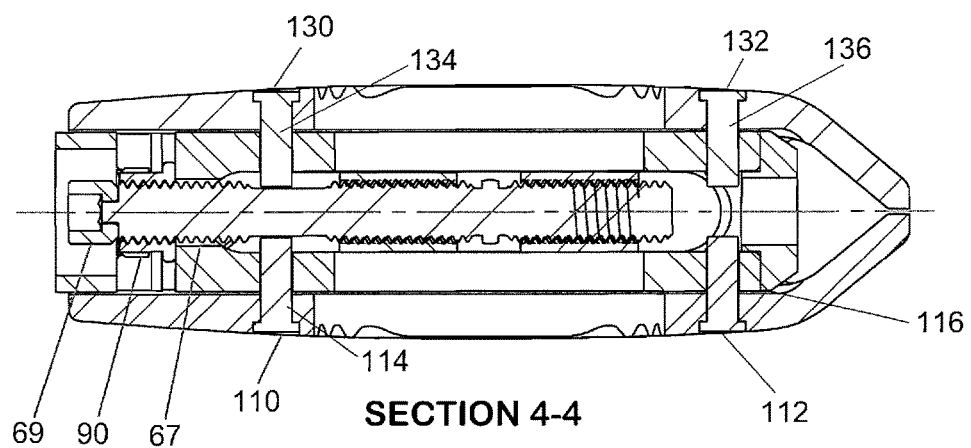
FIG. 4 is a cross sectional view of FIG. 3 taken along section line 4-4.
Figure 5:
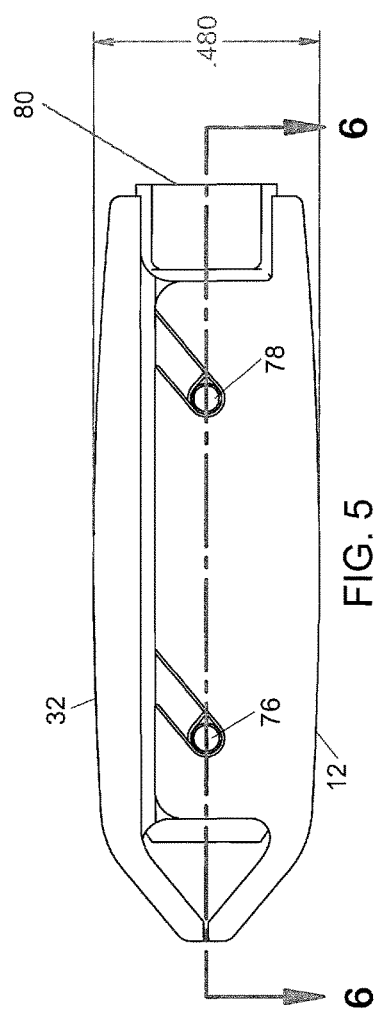
FIG. 5 is a side view thereof.
Figure 6:
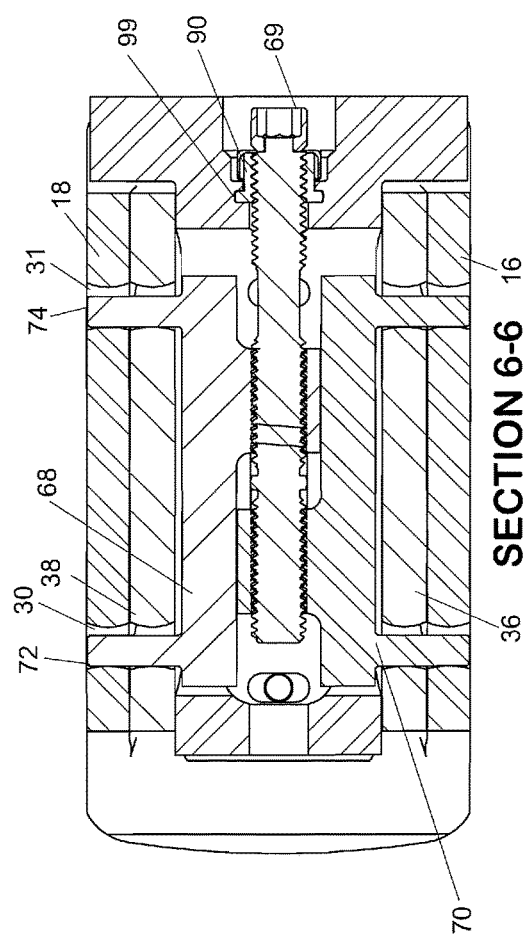
FIG. 6 is a cross sectional view of FIG. 5 taken along section line 6-6.
Figure 7:
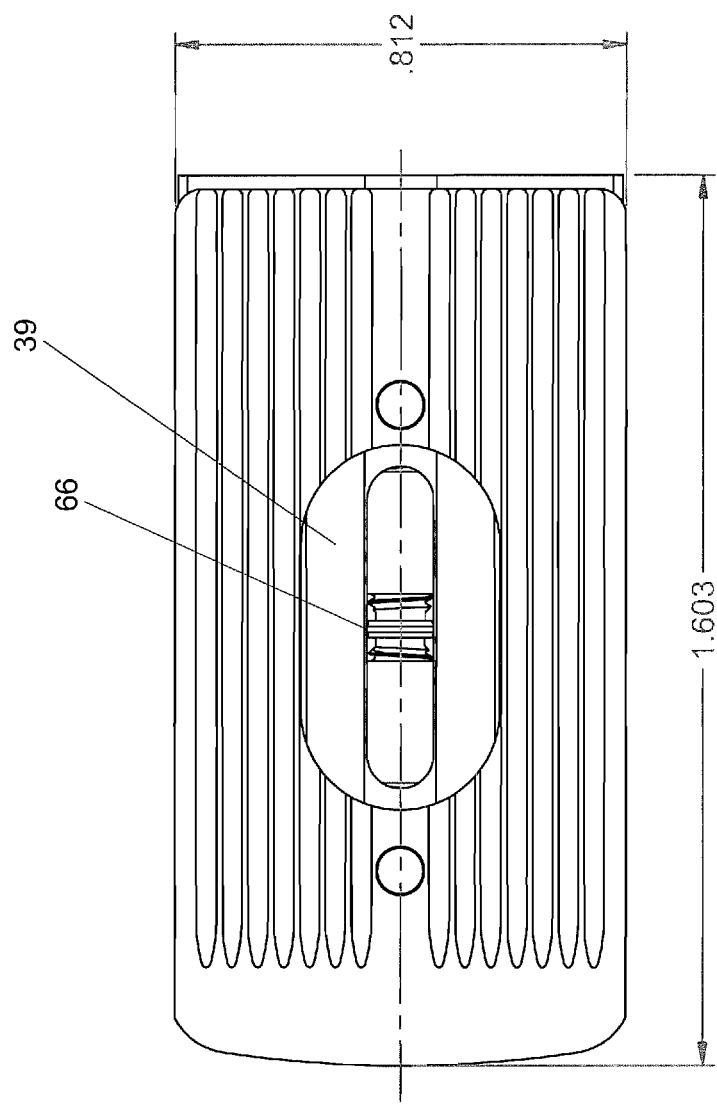
FIG. 7 is a top view thereof.
Figure 8:
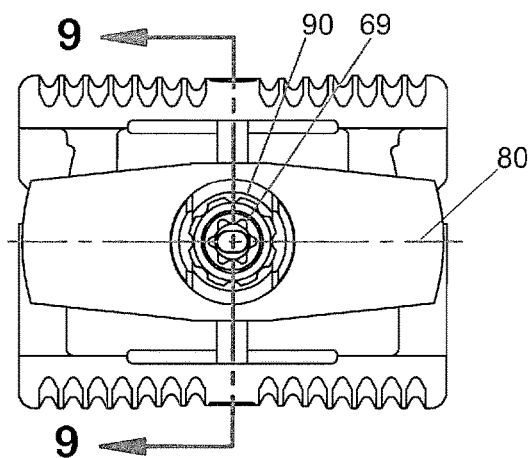
FIG. 8 is an end view of the spinal implant in an expanded position.

Referring to FIGS. 1-7, the lateral expanding coaxial spinal implant 10 employs a substantially rectangular bottom endplate 12 and top endplate 32, each having a grooved outer surface 13, 34 to engage bone. The bottom endplate 12 includes a first vertical outer sidewall 16 spaced apart from a second vertical outer sidewall 18. The first vertical sidewall 16 has a front bottom slot 20 placed at a predetermined angle defined by a lower end 22 and an upper end 24, and a rear bottom slot 26 placed at a predetermined angle defined by a lower end 28 and an upper end 29. The second vertical sidewall 18 forms a mirror image of the first vertical outer sidewall 16, including a front bottom slot 30 and rear bottom slot 31 having the same angular slope as the first vertical sidewall 16.

The top endplate 32 has a grooved outer surface 34 and a first vertical inner sidewall 36 spaced apart from a second vertical inner sidewall 38 constructed and arranged to be placed inboard, along an inner side surface of said bottom endplate sidewalls 16, 18, positioning sidewall 16 in relation to sidewall 36, and positioning sidewall 18 in relation to sidewall 38. The first inner sidewall 36 has a front slot 40 placed at a predetermined angle defined by a lower end 42 and an upper end 44, and a rear slot 46 placed at a predetermined angle defined by a lower end 48 and an upper end 50. The second inner sidewall 38 forms a mirror image of the first inner sidewall 36, with the same angular slope as the first inner sidewall 36. In the preferred embodiment, each of the angled slots are angled at about 45 degrees. However, the angle can be between 25 and 75 degrees for use with targeted applications. Bottom endplate 12 includes aperture 21, and top endplate 32 includes aperture 39 for receipt of bone or bone graft material. In the preferred embodiment, the front 20 and rear 26 angled slots of the bottom endplate 12 are angled from front 81 to rear 83, and the top endplate slots 40, 46 are angled from rear 83 to front 81.

A centrally located drive screw 60 has a shank with lead threads 62 and 64 on either side of a center section 66. The lead threads are formed clockwise and counterclockwise. Adjustment threads 67 are located along a driver end of the drive screw and include a driver nut cap 69 for receipt of a star, hex or Allen drive tool. The drive screw 60 has a rear threaded actuator 68 moved by rearward lead thread 64 with matching threads, and forward threaded actuator 70 moved by front lead thread 62. Front actuator 70 contains actuator pins 76 and 78 for placement through sidewall slots 20 and 26, and actuator pins 72 and 74 for placement through sidewall slots 30 and 31.

Similarly, front actuator 70 contains actuator pin 76 for placement through slots 20 and 40, and actuator pin 78 for placement through slots 26 and 46. The angular slots in each endplate are sloped to allow lateral expanded positioning of the outer surfaces of the endplate as the actuators are moved. The slots 20, 26, 40 and 46 are radiused to allow tilting of the actuators 68 and 70 without binding of the actuator pins.

A carriage 80 contains the drive screw 60 and supports actuators 68 and 70. The carriage 80 is T-shaped, having a centrally disposed aperture 84 with a formed cavity 86 for receipt of an adjustment nut 90. The adjustment nut 90 includes a lip 98 that is rotatable within a portion of the cavity 86, allowing rotation without axial movement. The carriage 80 further includes a bifurcated body 92 for the slidable positioning of the rearward actuator 68 and forward actuator 70; the rearward actuator 68 having a threaded boss 96 for engaging the forward lead thread 62, the forward actuator 70 having a threaded boss 99 for engaging the rear lead thread 64. A cap 149 is placed along an end of actuator 70 for engaging the drive screw 60.

The drive screw 60 is attached to the carriage 80 with adjustment nut 90 engaging threaded portion 67. The adjustment nut 90 is held to the carriage 80 to prevent axial movement. Rotational movement of the nut is provided having a lip 98 for placement with a containment section 97. The adjustment nut 90 is threaded for receipt of the drive screw 60. Rotation of the adjustment nut 90 causes axial translation of the drive screw 60, yet maintains a position against the carriage 80.

The lower endplate 12 includes first and second alignment pins 110, 112 which fit within alignment aperture 114 and 116 respectfully; the carriage 80 having a first lower slot 120 for receipt of alignment pin 110, and a second lower slot 122 for receipt of alignment pin 112. Similarly, the carriage 80 includes third and fourth alignment pins 130, 132 which fit within alignment apertures 134 and 136 respectfully; the carriage 80 having a first upper slot 138 for receipt of alignment pin 130, and a second upper slot 140 for receipt of alignment pin 132. The slots 120, 122, 138 and 140 are elongated to allow lateral rotation of the carriage a predetermined amount, yet prevent axial movement.

FIGS. 3-7 and 18 depict the spinal implant in a compressed position with minimal distance between the bottom surface 13 and the top surface 34. In the preferred embodiment, the compressed condition provides a height of about 0.480 inches, a width of about 0.812 inches, and a length of about 1.603 inches. In these illustrations, the adjustment nut 90 and driver nut cap 69 are in a position wherein rearward and forward actuators 68 and 70 are separated from the adjustment nut with pin 76 at the base of slots 20 and 40, pin 78 at the base of slots 26 and 46, and pins 72 and 74 at the base of mirror image slots 30 and 31 formed on the opposite sides of the endplates 12, 32. The position of the actuators 68 and 70 can be viewed through the aperture 39 in relation to the drive screw 60.

Figure 9:
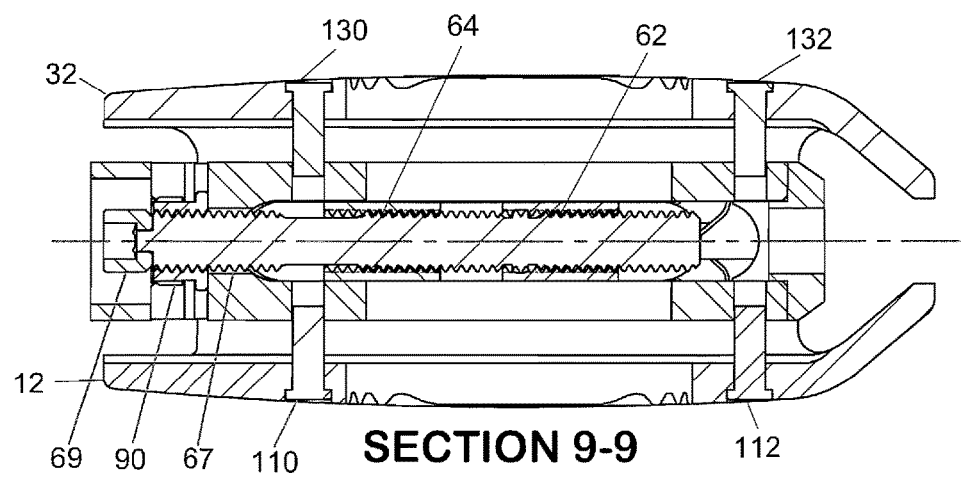
FIG. 9 is a cross sectional view of FIG. 8 taken along section line 9-9.
Figure 13:
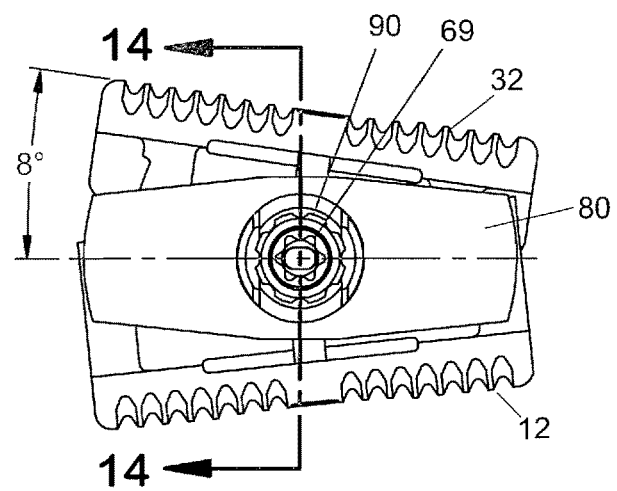
FIG. 13 is an end view of the spinal implant in an angular position.
Figure 14:
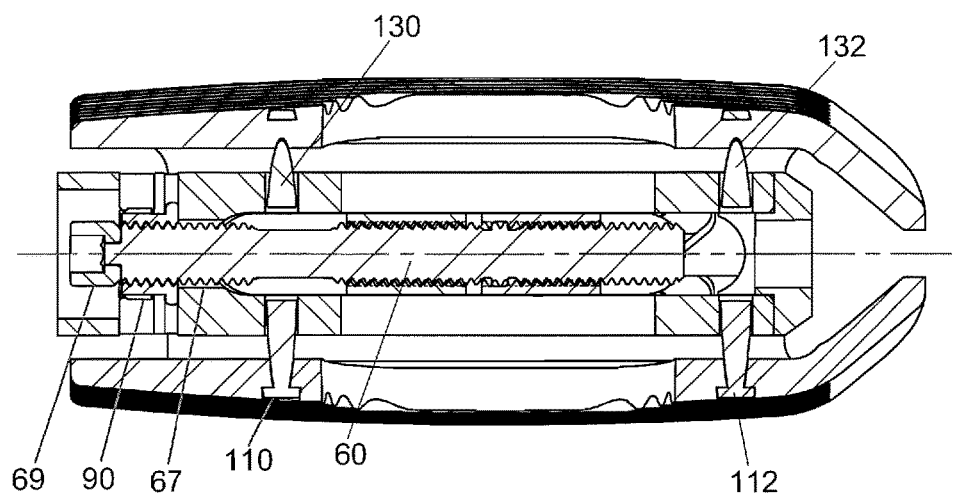
FIG. 14 is a cross sectional view of FIG. 13 taken along section line 14-14.
Figure 15:
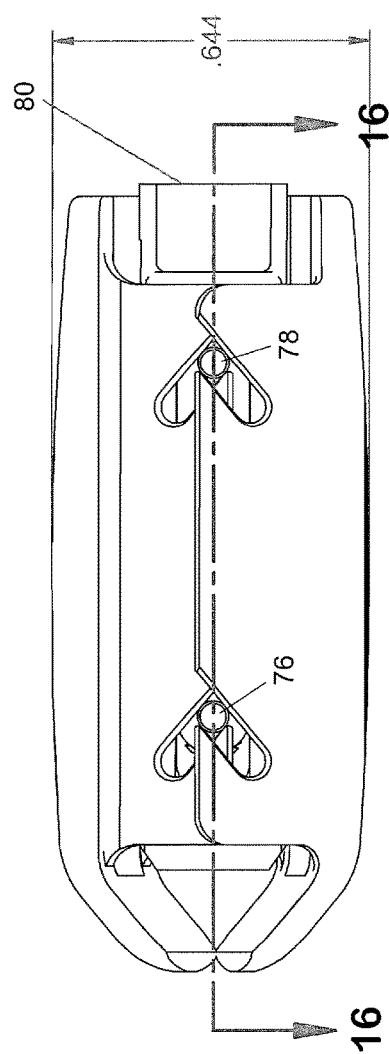
FIG. 15 is a side view thereof.
Figure 16:
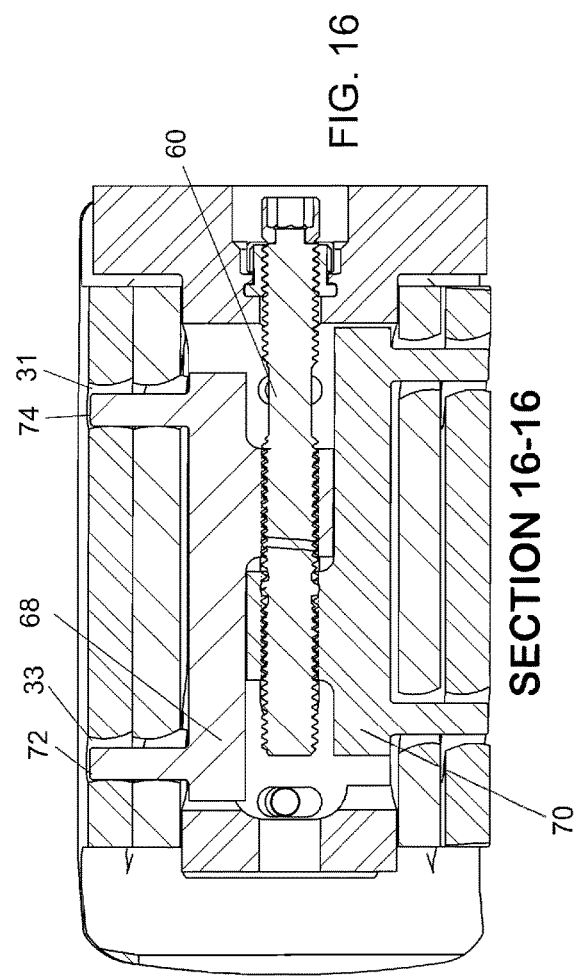
FIG. 16 is a cross sectional view of FIG. 15 taken along section line 16-16.
Figure 17:
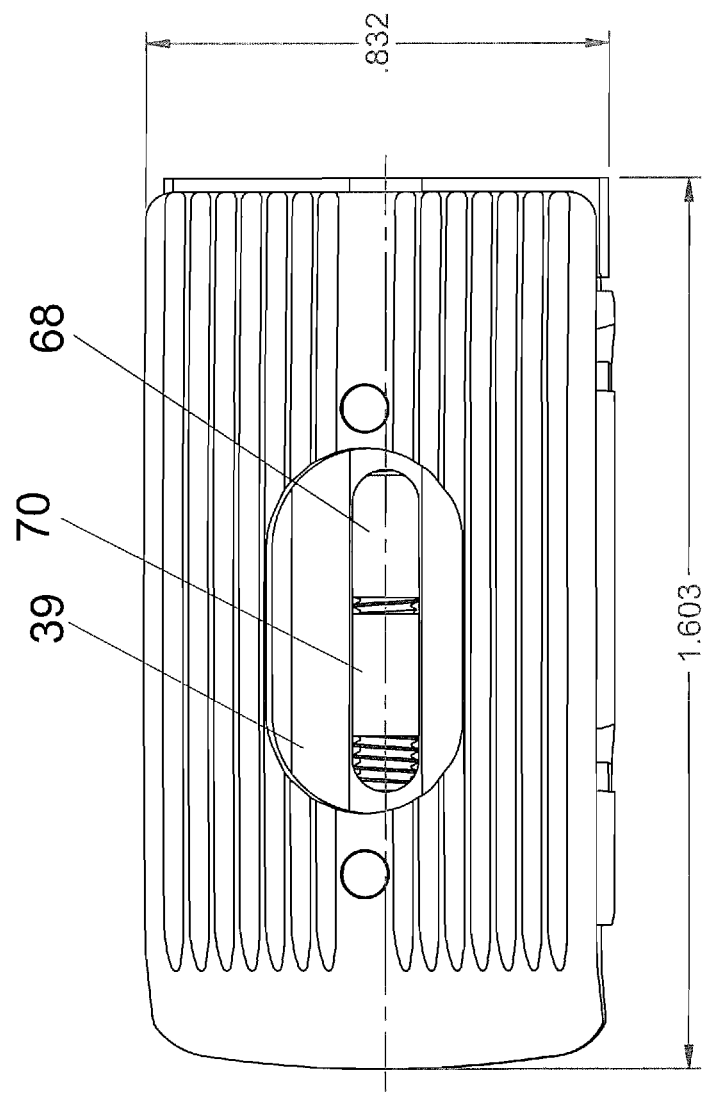
FIG. 17 is a top view thereof.
Figure 18:
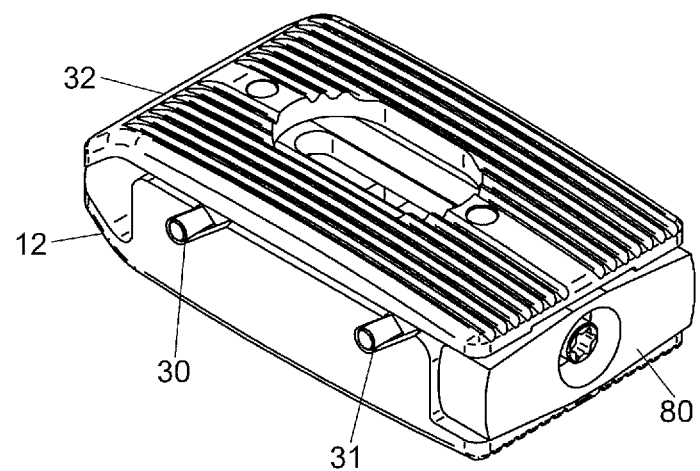
FIG. 18 is a perspective view of the spinal implant in the compressed position.
Figure 19:
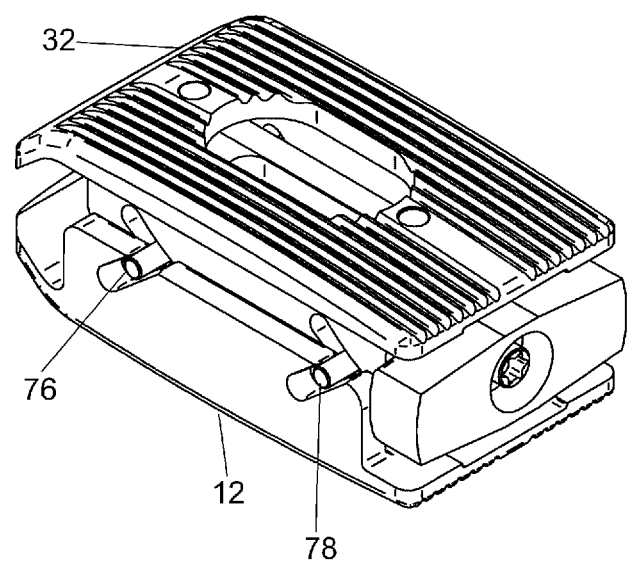
FIG. 19 is a perspective view of the spinal implant in the expanded position.
Figure 20:
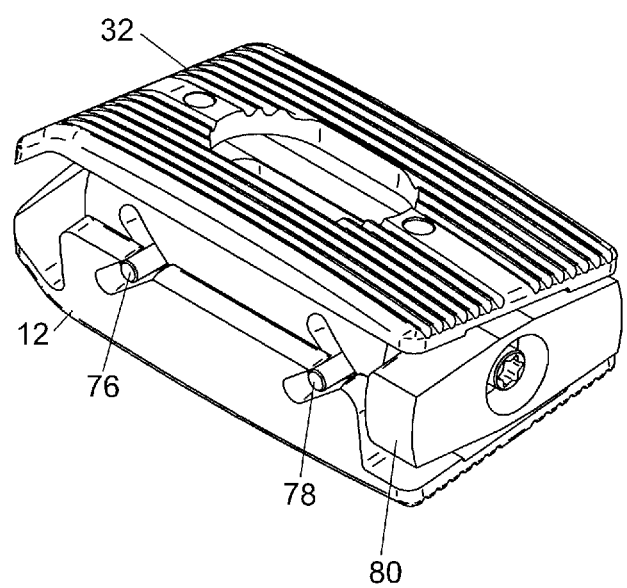
FIG. 20 is a perspective view of the spinal implant in the angular position.

FIGS. 8-12 and 19 depict the spinal implant in an expanded position with a maximum distance between the bottom surface 13 and the top surface 34. In the preferred embodiment, the expanded condition provides a height of about 0.632 inches; the width and length remain the same. In these illustrations, the adjustment nut 90 and driver nut cap 69 have been rotated, causing rearward and forward actuators 68 and 70 to be drawn toward the adjustment nut with pin 76 drawn across slots 20 and 40, pin 78 drawn across slots 26 and 46 on one side, and pins 72 and 74 drawn across mirror image slots formed on the opposite sides of the endplates 12, 32. Movement of the actuators 68 and can be viewed through the aperture 39 in relation to the drive screw 60. As depicted in FIG. 9, the alignment pins 110, 112, 130 and 132 are depicted in a raised condition and within the respective alignment slots.

FIGS. 13-17 and 20 depict the spinal implant in a lateral angular tilt of about 8 degrees. In the preferred embodiment, the angular position provides a height of about 0.644 inches at the highest angle edge, the width is about 0.832 inches and the length remains the same, about 1.603 inches. In these illustrations, the adjustment nut 90 and driver nut cap 69 have been rotated, causing rearward and forward actuators 68 and 70 to be drawn toward the adjustment nut with pin 76 drawn across slots 20 and 40, pin 78 drawn across slots 26 and 46 on one side, and pins 72 and 74 drawn across mirror image slots formed on the opposite sides of the endplates 12, 32. Movement of the actuators 68 and 70 can be viewed through the aperture 39 in relation to the drive screw 60. As depicted in FIG. 9, the alignment pins 110, 112, 130 and 132 are depicted in a raised condition and within the respective alignment slots. Rotation of adjustment nut 90, without rotation of the driver nut cap 69, causes the lateral movement of the endplates 12 and 32, allowing surfaces 13 and 34 to be placed up to about an 8 degree angle. Rotation of the adjustment nut 90 can provide lateral movement of the endplates 12, 32 in either a left hand direction providing a −8 degree angle from top center, to a right hand direction providing a +8 degree angle from top center in relation to the carriage 80.

To evenly expand or contract the endplates 12 and 32, the drive screw 60 and adjustment nut 90 are rotated together, with no relative motion between them. To change the angle of the endplates 12 and 32, the driver nut cap 69 is rotated while keeping the adjustment nut 90 fixed, or the adjustment nut 90 can be rotated and the drive screw 60 fixed. In one embodiment, rotation of the adjustment nut 90 moves the actuators 68, 70, wherein the pins engage the slots to cause lateral movement of the bottom and top endplates 12, 32. In this embodiment, the adjustment nut 90 repositions the actuators in respect to the carriage 80, wherein the actuator pins 72, 74, 76 and 78 engage the slots 20, 26, 40 & 46 resulting in angular positioning of the bottom 12 and top 32 endplate.

The spinal implant of the present invention may be comprised of any suitable non-bone composition, including but not limited to metal, polymer compositions (e.g. poly-ether-ether-ketone (PEEK) and/or poly-ether-ketone-ketone (PEKK)), ceramic, or any combination of these materials.

Figure 21:
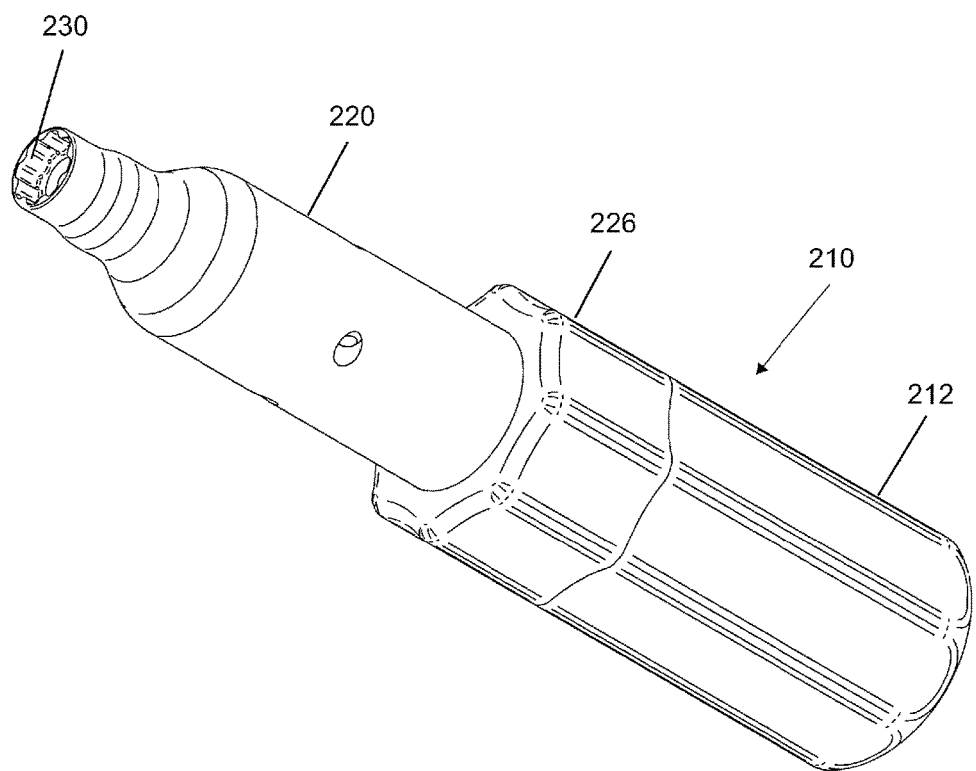
FIG. 21 is a perspective view of the instrument driver.
Figure 22:
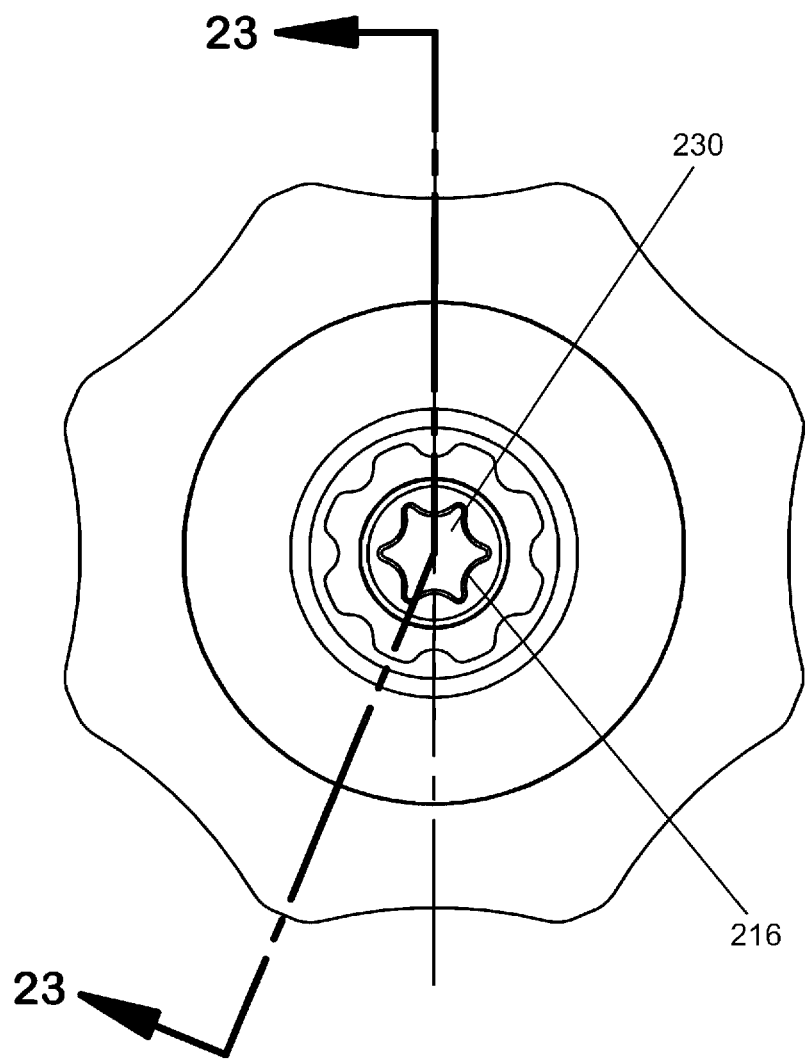
FIG. 22 is an end view of the instrument driver.
Figure 23:
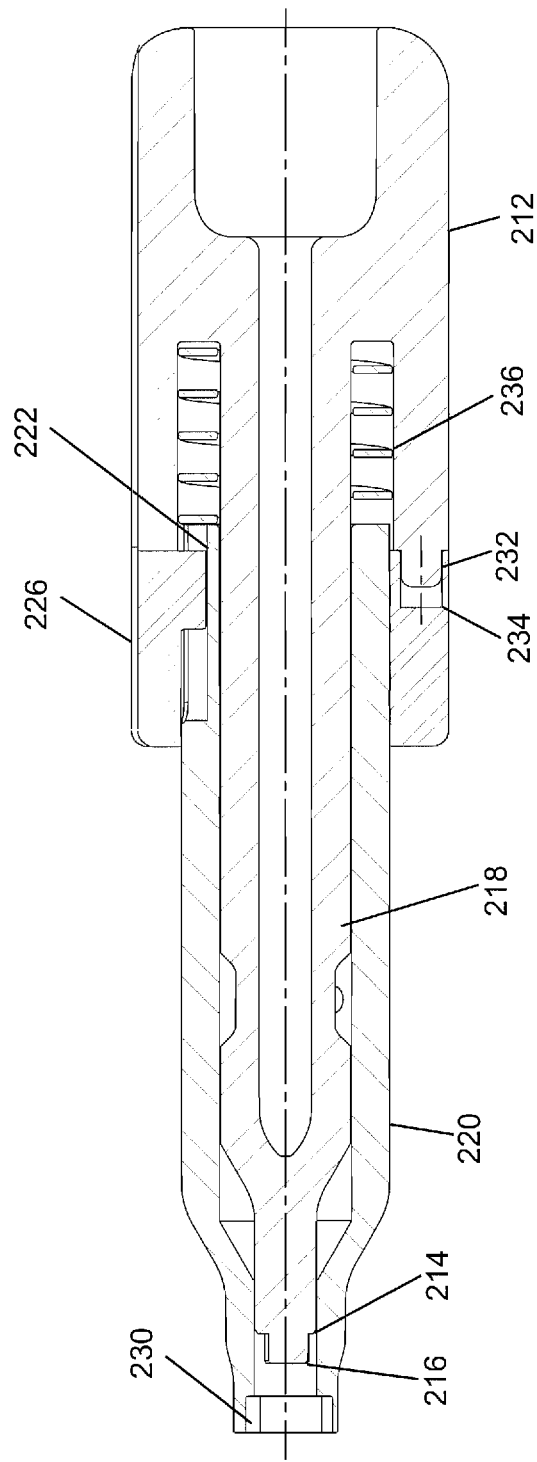
FIG. 23 is a cross sectional side view taken along section line 23-23 of FIG. 22.

Referring now to FIGS. 21-23, illustrated is the instrument driver 210 for use in installing the implant 10. The instrument driver 210 engages the driver nut cap 69 of the drive screw 60 and adjustment nut 90, wherein the drive screw 60 and adjustment nut 90 can be rotated simultaneously or independently, adjusting the height and lateral angular position of the endplates 12, 32. The driver instrument 210 is formed from a base 212 sized to allow gripping by an individual on one end and a driver head 214 connected thereto having a star tip driver 216 for rotating of the driver nut cap 69. In the preferred embodiment, the base 212 and shaft 218 are connected to assure rotational movement is one piece. An extendable sleeve 220 having a proximal end 222 is slidably securable to the base 212 using a slide collar 226. The slide collar 126 engages the base 212 to allow simultaneous rotation of an adjustment nut socket 230 when the slide collar 226 engages the base 212. When the slide collar 226 is detached from the base 212, only the base 212 is engaged to cause rotation of the star tip driver 216. The base 212 has a plurality of engagement tabs 232 to interlock with receptacles 234 located along the perimeter of the slide collar 226; the slide collar 226 having at least one spring 236 to bias the slide collar 226 with the base 212.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A lateral expanding coaxial spinal implant system comprising:
   a substantially rectangular bottom endplate having first and second outer sidewalls, each said sidewall including a front and rear slot angled away from a front end of said bottom endplate;
   a substantially rectangular top endplate having first and second inner sidewalls, each said sidewall including a front and rear slot angled away from a rear end of said top endplate;
   a carriage positionable between said inner and outer sidewalls with a centrally disposed aperture, said aperture including a cavity for receipt of an adjustment nut;
   a drive screw rotatably formed from a shank insertable into said carriage aperture with adjustment threads for securement to said adjustment nut, said drive screw having clockwise threads formed along a first portion and counterclockwise threads formed along a second portion;
   a first actuator threadably attached to said first portion of said drive screw, said first actuator including a forward pin and a rearward pin operatively associated with slots formed in said first inner and said first outer sidewalls;
   a second actuator threadably attached to said second portion of said drive screw, said second actuator including a forward pin and a rearward pin operatively associated with slots formed in said second inner and said second outer sidewalls;
   whereby simultaneous rotation of said drive screw and said adjustment nut moves said actuators in unison, wherein said pins engage said slots to cause equal separation of said bottom and top endplates;
   whereby rotation of said adjustment nut, without rotation of said drive nut cap, repositions said actuators to cause lateral rotation of said bottom and top endplate.

2. The lateral expanding coaxial spinal implant system according to claim 1, wherein each said endplate includes alignment pins engaging said carriage, said alignment pins maintaining axial position of said endplates to said carriage.

3. The lateral expanding coaxial spinal implant system according to claim 2, wherein each said carriage includes lateral slots for receipt of said alignment pins, said lateral slots allow lateral rotation of said endplates up to about 8 degrees in relation to said carriage in a first direction and up to about −8 degrees in relation to said carriage in a second direction.

4. The lateral expanding coaxial spinal implant system according to claim 1, wherein an outer surface of each said endplate has a plurality of grooves constructed and arranged to engage bone.

5. The lateral expanding coaxial spinal implant system according to claim 1, wherein each said outer surface of each said endplate includes an aperture for receipt of bone material.

6. The lateral expanding coaxial spinal implant system according to claim 1, wherein cavity in said carriage includes a containment section for receipt of a lip formed on said adjustment nut, said containment section allows rotation of said adjustment nut without axial movement.

7. The lateral expanding coaxial spinal implant system according to claim 1, wherein said drive screw includes a cavity in said carriage having a containment section for receipt of said lip formed on said adjustment nut, said containment section allows rotation of said adjustment nut without axial movement.

8. The lateral expanding coaxial spinal implant system according to claim 1, including a driver nut cap secured to said drive screw.

9. The lateral expanding coaxial spinal implant system according to claim 8, wherein said driver nut cap is constructed and arranged to permit rotation of said adjustment nut and said drive screw with a single tool.

10. The lateral expanding coaxial spinal implant system according to claim 8, wherein said driver nut cap is removable.

11. The lateral expanding coaxial spinal implant system according to claim 1, wherein said drive screw and adjustment nut can be rotated simultaneously or independently by an instrument driver comprising:
   a base being formed from a base to allow gripping by an individual on one end and a driver head for rotating of said drive screw on an opposite end;
   an extendable sleeve having a proximal end slidably securable to said base using a slide collar, said slide collar engaging said base to allow simultaneous rotation of said adjustment nut and said drive screw when said slide collar is attached to said base, said base to allow only rotation of said adjustment nut when said collar is detached from said base.

\* \* \* \* \*